United States Patent [19]

Percarpio et al.

[11] Patent Number: 4,886,072
[45] Date of Patent: Dec. 12, 1989

[54] MULTIPLE SAMPLE NEEDLE ASSEMBLY WITH VEIN INDICATOR

[75] Inventors: Edward P. Percarpio, North Haledon; Andrzej J. Plucinski, Norwood, both of N.J.

[73] Assignee: Becton, Dickinson and Company, Franklin Lakes, N.J.

[21] Appl. No.: 562,309

[22] Filed: Dec. 16, 1983

[51] Int. Cl.$^4$ ............................................. A61B 5/14
[52] U.S. Cl. .................................. 128/763; 128/765; 128/766
[58] Field of Search .............. 128/760, 763, 765, 776, 128/771

[56] References Cited

U.S. PATENT DOCUMENTS

| | | | |
|---|---|---|---|
| 3,985,616 | 10/1976 | Weaver et al. | 195/63 |
| 4,207,870 | 6/1980 | Eldridge | 128/766 |
| 4,340,067 | 7/1982 | Rattenborg | 128/763 |
| 4,416,291 | 11/1983 | Kaufman | 128/766 |
| 4,519,402 | 5/1985 | Andersen | 128/765 |

Primary Examiner—Max Hindenburg
Assistant Examiner—J. P. Lacyk
Attorney, Agent, or Firm—Robert P. Grindle

[57] ABSTRACT

A multiple liquid sample needle assembly is provided. The assembly includes a housing with a sample receiving chamber having translucent or transparent walls for determining whether access to the sample source in question has been obtained. The invention utilizes a highly absorbent material in a form which allows venting of gases displaced from the housing chamber by the liquid sample being obtained, which material expands upon contact with the liquid sample to provide a liquid impervious barrier. The improvement in this invention is the absorbent material in a separate sleeve-like form which may be a laminate or a compacted tablet sleeve of the absorbent material for rapid and easy insertion between the two hub parts forming the assembly housing. The arrangement herein is particularly appropriate for mass production techniques in that two housing parts may have inserted therein the tablet sleeve of the invention, rather than as in previous approaches where an absorbent material similar to that utilized herein in a sleeve or tablet like form was introduced in a loose non-precise powder form for a relatively imperfect seal between two housing parts. The invention herein contemplates sonic welding, gluing, or snap fitting of the housing parts together in a further production line procedure.

14 Claims, 6 Drawing Sheets

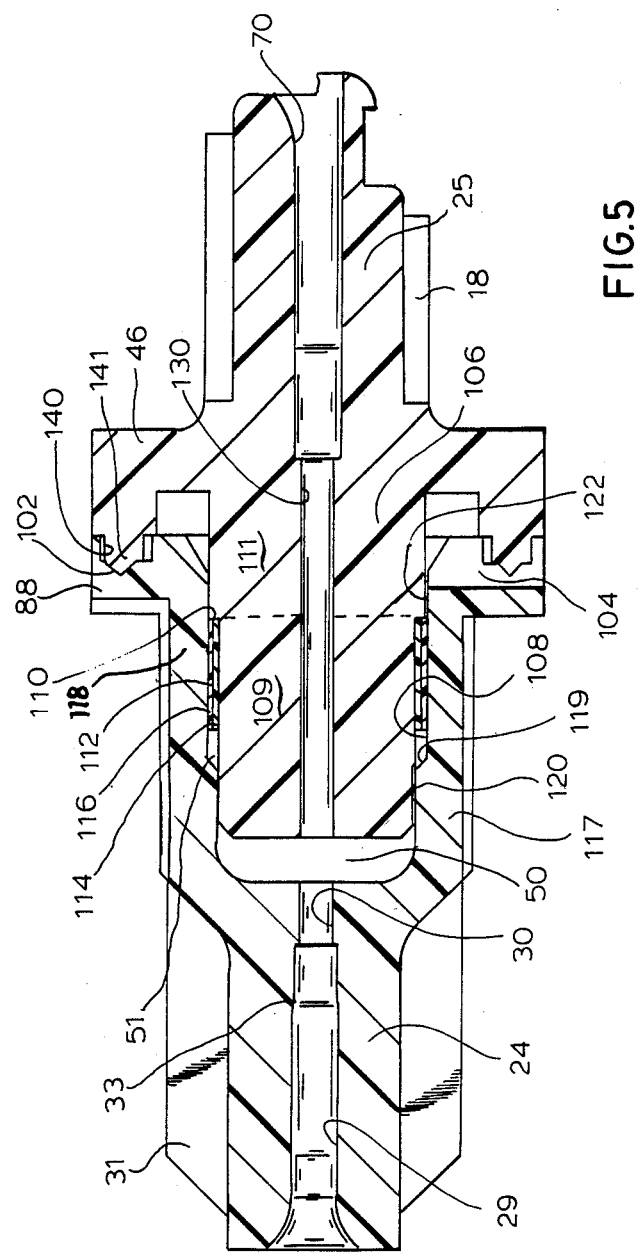

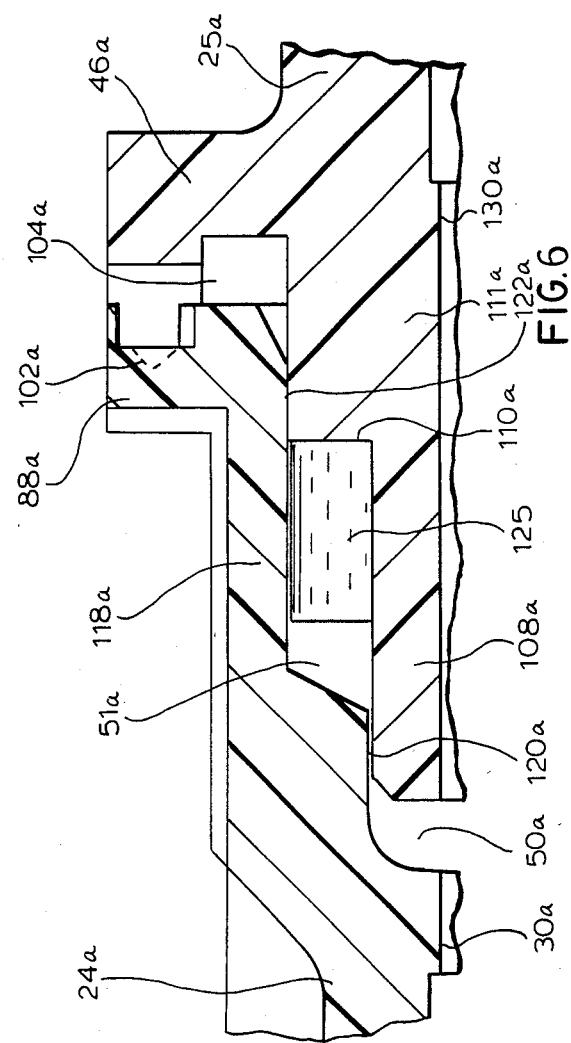

MULTIPLE SAMPLE NEEDLE ASSEMBLY WITH VEIN INDICATOR

BACKGROUND AND STATEMENT OF THE INVENTION

This invention relates to an assembly for collecting a liquid sample from a patient, such as a blood sample. More particularly, this invention relates to a needle assembly for collecting single and multiple liquid samples from such a patient with the use of the single assembly herein. The device of the invention utilizes a housing chamber for the samples with walls which are translucent or transparent, for visually indicating whether or not proper access to the sample source in question has been achieved.

Moreover, a material which is highly absorbent to aqueous containing solutions is utilized in the form of a substantially cylindrical sleeve in a form providing air passage so that gas displaced by a liquid sample moving into the housing chamber may be vented, followed by an immediate swelling of the material upon exposure of the liquid sample to prevent any discharge of the liquid sample from the housing chamber. For example, the sleeve may be comprised of a solid compacted material which is of a size allowing an air bleed passage between the outer walls of the sleeve and the adjacent walls of the housing containing the sleeve. The material swells on contact with the liquid closing the bleed passage or passages.

As an alternative arrangement herein, a sleeve in the form of a laminate may be provided with the laminate comprised of three layers. The inner layer is the swellable material, while the two outer layers are in the form of fabric-like non-woven sheet material with sufficient porosity to allow the initial bleeding of air, as discussed above.

Thus, the tablet or laminated material forming the cylindrical sleeve of the invention seals the chamber against discharge of the sample, while simultaneously providing for the venting of gas displaced by that same sample. Once entry has been made to the source of the liquid sample, as indicated by the transparent or translucent chamber walls visually showing the presence of the sample in the housing chamber, then multiple samples may be collected from the housing chamber by being drawn sequentially into a plurality of vacuum collection devices. The assembly incorporates a separate flexible self-sealing elastomeric sleeve which cooperates with the discharge opening of the device during periods of exchange of the vacuum collection devices for sequential discharge of additional samples.

As discussed above, it is desirable to provide a mechanism whereby the user of such a needle assembly can be informed when the intravenous needle has penetrated the source of the sample to be obtained, such as the vein of the patient for collection of a blood sample. Many times in collecting blood from a patient, it is difficult to locate the vein, or for other reasons blood flow into the collecting device is not adequate. In those instances, it is advantageous to be able to make a quick determination that entry into the vein has been made, and that blood is flowing into the needle assembly. Once this determination has been made and the vein entry achieved, the evacuated blood collection containers can be inserted into the collection assembly in accordance with well known techniques of collecting blood samples during a collection procedure involving a single vein entry.

The invention here is arranged to overcome one of the problems which arises during the veni-puncture step in that pockets of air are present in the various needle assemblies. When veni-puncture is made, and the evacuated blood collection container is not yet attached to the opposite end of the structure, blood cannot flow into the needle assembly because of a pocket of air which, under normal atmospheric conditions, remains inside the needle assembly. Thus, even though vein entry may have been accomplished, blood flow may not begin, simply because of the air pocket blockage in the assembly.

With this invention, by contrast, through the utilization of a venting arrangement adjacent the housing chamber, the sleeve of the invention allows for displacement of the air from the housing chamber so as to allow room for receiving the blood sample being collected. Thus, as the blood is simultaneously moving into the chamber of the housing, air is being vented through the sleeve of the invention. At the moment when the blood comes into contact with the sleeve, the sleeve expands rapidly by absorbing the aqueous content of the blood sample, and prevents any further venting through the sleeve of the invention.

Both U.S. Pat. Nos. 4,207,870 and 4,398,544, assigned to the common assignee herewith, utilize a porous plug in blood collection assemblies of the kind described herein. Both of these arrangements utilize a material which is air pervious and liquid impervious. The material is a sintered material and the material is occluded by the movement of a blood sample into the interstices of the porous material. Both patents describe inventions utilizing relatively complicated valve structures, including movable internal parts. Although the inventions recognize the utilization of a porous material for providing a venting for displaced air during receiving a blood sample, there is still room for improvement over such a device and particularly with respect to the present invention wherein the material is in the form of a separate sleeve or tablet which may be inserted in a mechanical manner between the two parts forming a housing during the construction thereof in a production line. That is, absolute positive sealing may not always be achieved merely by physical occlusion, although generally such procedures are effective.

By contrast, the arrangement herein is a simplified structure comprising a highly absorbent material in the form of a sheet, which swells in contact with aqueous substances, in combination with a porous non-woven tape material, which non-woven material may be incorporated with the highly absorbent sheet material to form a sleeve arrangement positioned between the two parts of the housing forming the multiple sample device herein. Alternatively, and preferably, the material is in the form of a tablet of the highly absorbent material compressed from that material into a sleeve-like cylindrical tablet form, which is inserted mechanically between the two parts forming the housing. As will be understood by practitioners-in-the-art of constructing multiple blood collection assemblies, these cylinders may be formed separately in large numbers for insertion in a mass production line between the two parts forming the housing, with all such procedures being handled by robots.

Before describing this invention in more detail, it may be well to note that the material forming the substantially cylindrical vent sleeve of the invention may be comprised of a hydrolyzed starch-polyacrylonitrile graft copolymer with side chains containing carboxamide and carboxylate groups, such as WATER-LOCK-A100, a product of Grain Processing Corporation, 1600 Oregon Street, Muscatine, Iowa 5276. Other sources include Henkel Corporation, 4620 West 77th Street, Minneapolis, Minn., Super Absorbent Company, Route 3, P.O. Box 342, Lumberton, N.C. and Edison Hydrocontrol Chemicals Inc., 99 Madison Avenue, New York, New York 10016.

The absorbent polymeric compositions of the invention may be prepared by the procedures taught in U.S. Pat. No. 4,045,387; 4,134,863; 3,981,100; 4,159,260; 3,661,815; 3,935,099; and 3,985,616.

Other objects and advantages of this invention will be apparent from the following description, the accompanying drawings and the appended claims.

DETAILED DESCRIPTION OF THE DRAWINGS

FIG. 5 is an enlarged sectional view of the housing assembly of FIG. 1 with the cannulas removed, and showing the two-part assembly of the housing in the form of a intravenous hub and a negative pressure hub having formed therebetween one embodiment of the sleeve of the invention;

FIG. 6 is a partial sectional view of the two housing parts as shown in FIG. 5, and illustrating a further embodiment of the invention in the form of a compressed tablet sleeve.

DETAILED DESCRIPTION OF THE DRAWINGS

Figure 1:
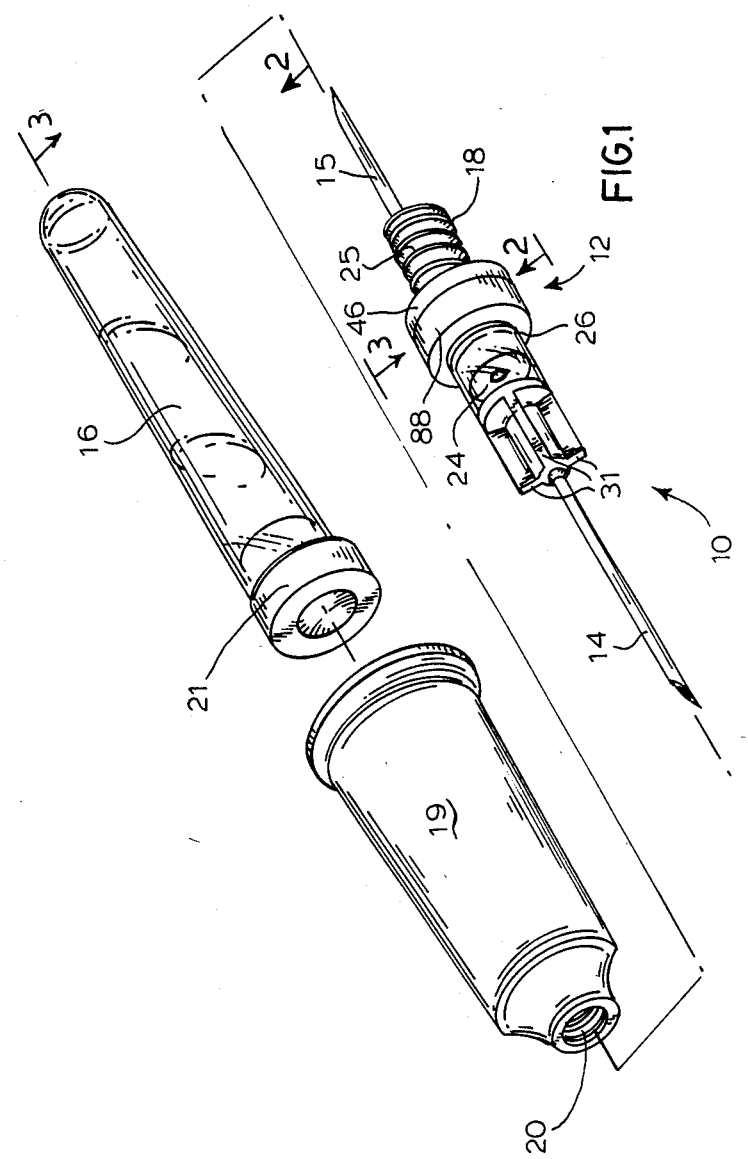
FIG. 1 is an exploded perspective view illustrating generally the standard parts and arrangements of a sample collection needle assembly, including a holder for an evacuated container and an evacuated blood collection container for use in obtaining blood samples from a patient.

Referring to the drawings in which like reference characters refer to like parts throughout the several views thereof, FIG. 1 shows the basic external components of needle assembly 10, including a housing 12, a first intravenous (I.V.) needle cannula 14 adapted for insertion into a patient and a second negative pressure needle cannula 15 at the opposite end of housing 12. The second needle cannula 15 is adapted for penetration into an evacuated container 16 for collection of a blood sample. Housing 12 includes a negative pressure hub portion 25 having threads 18 adjacent the second cannula 15 onto which a container holder 19 is threaded by its internal mating threads 20 at the forward end of the holder. Evacuated container 16 is inserted into holder 19 so that second needle cannula 15 penetrates the stopper 21 at the forward end of the evacuated container 16. These general aspects of blood sample collection assemblies are well known to those skilled in the art.

Figure 2:
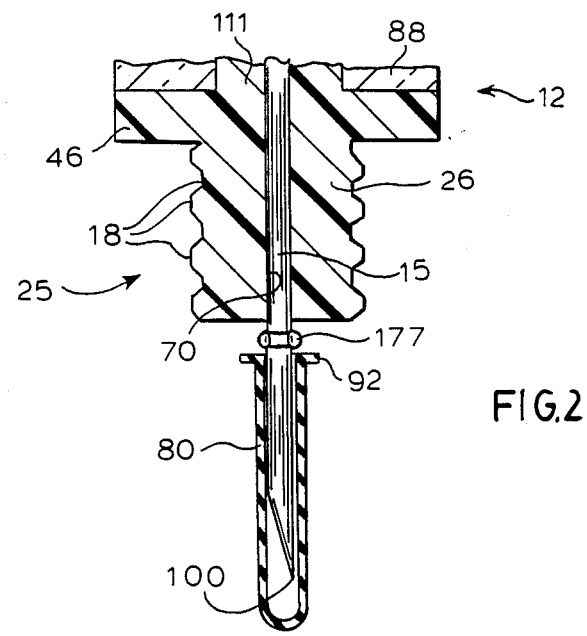
FIG. 2 is a partial enlarged cross-sectional view taken along lines 2—2 of FIG. 1 and illustrating the separate elastomeric sleeve valve utilized in the assembly herein.
Figure 4:
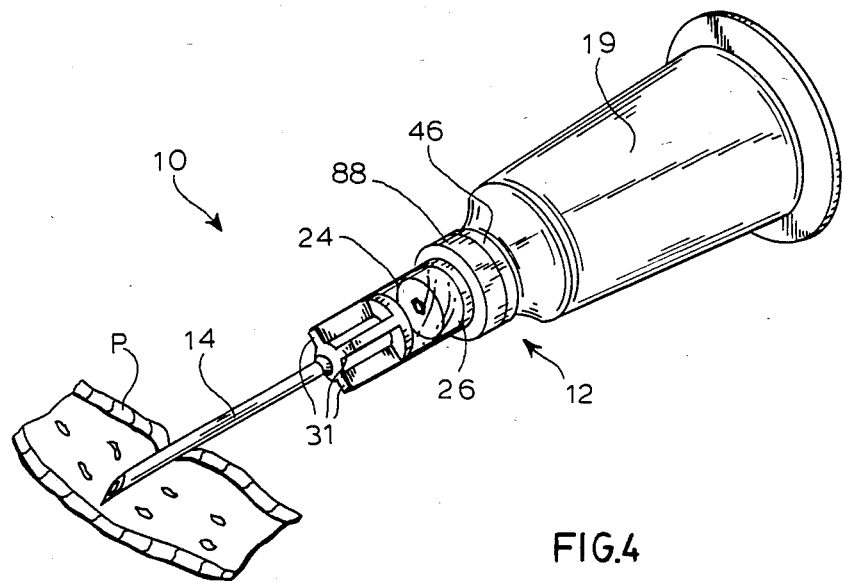
FIG. 4 is a perspective view of a needle assembly connected to a holder inserted into a patient so that a user can view the assembly for indication of vein entry.

Referring now to FIG. 2, negative pressure hub end 25 of housing 12 is shown, and includes a cylindrical portion 111 for cooperation with a bore in the forward intravenous hub 24 to be described below. A flange 46 is arranged to cooperate with a flange 88 on the forward I.V. hub, again as to be described below. A bore 70 extends through the rearward end 25 of he housing. Bore 70 is sized to accept the diameter of second needle cannula 15, which is secured to bore 70 by appropriate means such as adhesives, for example. It is within the purview of the invention, as will be described in more detail below that the two hubs may be joined together by sonic welds.

Figure 3:
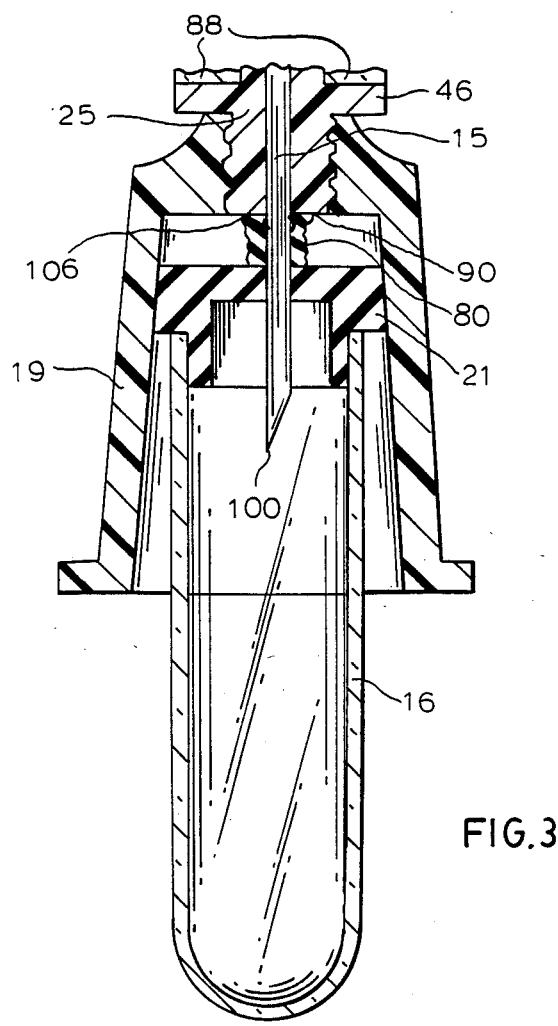
FIG. 3 is a partial enlarged cross-sectional view taken along lines 3—3 of FIG. 1.

As can be seen in FIG. 2, negative pressure cannula 15 ends in a point 100 which is arranged to penetrate the stopper 21 of an evacuated container 16. Covering the negative pressure end of cannula 15 is a self-sealing elastomeric sleeve 80 having a flange 92 thereon. Thus, when point 100 is forced into and through the central penetrable diaphragm of stopper 21, point 100 first penetrates the end of flexible sleeve 80 and forces sleeve 80 to collapse, as shown in FIG. 3. In this position, the upper flange 92 of sleeve 80 engages the bottom surface 106 of rear extension 26 of negative pressure hub 25. In this connection, the internal surface of flange 92 adjacent cannula 15 includes an abutment for engaging annular abutment 177 on cannula 15. This provides for a snap-fit engagement of sleeve 80 on cannula 15.

Referring now to FIG. 5, one embodiment of the invention is shown in the form of a laminate including the water absorbent material, such as an absorbent tissue designated A175, a product of Grain Processing Corporation, as noted above. It is a super absorbent laminate of its own, and is coupled with a two-sided tape material for forming the sleeve of the invention.

Thus, I.V. hub 24 includes a bore 29 therein for receiving I.V. cannula 14. Hub 24 includes a rear extension 117 of larger diameter, and which defines a housing chamber 50 therein for receiving a blood sample. Integrally formed at the rear of extension 117 is a further cylindrical portion 118 of the same outer diameter as portion 116, but having a larger internal bore 108 forming an offset 119 at the juncture of chamber 50 and bore 108.

Forming a communication between bore 29 and chamber 50 is a bore 30 of smaller diameter than bore 29. The offset 33 between bores 29 and 30 serves as a seat for the internal end of I.V. cannula 14. Surrounding the forward portion of hub 24 are a plurality of ribs 31 which cooperate with internal ribs on a shield, not shown, conventionally utilized to cover the intravenous cannula 14, until such time as it is to be used.

Negative pressure hub 25, forward of the flange 46, includes an integral cylindrical forward extension 111, followed by a further forward integral cylindrical extension 109. Extension 109 is of lesser diameter than portion 111 to define an offset 110 therebetween. Extension 109 cooperates with rear extensions 117, 118 of intravenous hub 24 to define a bleed passage 120, and an annular chamber 51. Annular chamber 51 defines the area for receiving the sleeve laminate of the invention which is mounted through the utilization of a double-sided adhesive tape 114, and the laminate absorbent material 116 of the invention. As discussed above, the laminate absorbent may be WATER-LOCK A-175, a product of Grain Processing Corporation. As can be seen in FIG. 5, the sleeve of the invention may be formed and mounted on the extension 109 of the negative pressure hub 25 prior to its insertion into the rear extension 117, 118 of I.V. hub 24.

Referring further to FIG. 5, it can be seen that mid-extension 111 of negative pressure hub 25 has a diameter slightly smaller than the diameter of bore 108 in order to define a vent passage at 122 which communicates with a vent 104 arranged in flange 88 forming the extreme rear end of I.V. hub 24. Flanges 46, 88, may be joined together to hold the entire assembly together by a sonic weld at 102. It will be appreciated by practitioners-in-the-art, however, that cooperating groove 140 and extension 141 formed in cooperating flanges 46, 88 may be joined together by an adhesive material, for example.

In considering generally the conditions for carrying out the invention herein it should be noted that the two-sided tape 114 is a product of the 3M Company and is a medically approved double-sided adhesive tape. The thickness of the L175 laminate is within the range of 0.035-0.040 inches, without compression. The laminate contains the superabsorbent polymer material as described above between two non-woven fluid permeable sheets.

As purely illustrative of dimensions herein, passage 120 between chamber 50 and chamber 51 is 0.003 inches wide. That is, extension 109 has a diameter of 0.157 inches while the diameter of chamber 50 defined by annular extension 117 on I.V. hub 24 is 0.160 inches. Again, bleed passage 122 is 0.003 inches. That is, the diameter of extension 111 is 0.177 inches while the diameter of bore 108 is 0.180 inches. With these dimensions in mind, it will be appreciated that the dimension of chamber 51 is 0.0125 inches. The length of the sleeve 112 is within the range of between about 0.08 and 0.10 inches.

Referring now to FIG. 6, a further preferred embodiment of the invention is shown wherein the sleeve 125 of absorbable material is in the form of a compressed tablet sleeve comprised of a compacted powder, compacted in a die to a density of about 2.2 grams per cubic centimeter (g/cc). The powder is designated WATER-LOCK TM A-100 a product of Grain Processing Corporation, manufactured under one or both of U.S. Pat. No. 3,661,815 or 4,159,260. The material is a starch-graft copolymer of polyacrylic acid and polyacrylamide. It has a density prior to compacting into the tablet sleeve of the invention of 0.307 grams per cubic centimeter. The WATER-LOCK A-100 is representative only of one product which may be used in forming the sleeve 125 of the embodiment shown in FIG. 6. In FIG. 6, the parts which are similar to the parts in the embodiment shown in FIG. are designated with the same number, except for the additional designation a. Thus, I.V. hub is designated 24a, and negative pressure hub is designated 25a. As will be appreciated, the radial extent of cavity 51a is larger than the radial extent of cavity 51 in the embodiment shown in FIG. 5 since the dimensions of the tablet sleeve 125 is thicker in radial extent than the laminate structure shown and described in the embodiment in FIG. 5.

Figure 7:
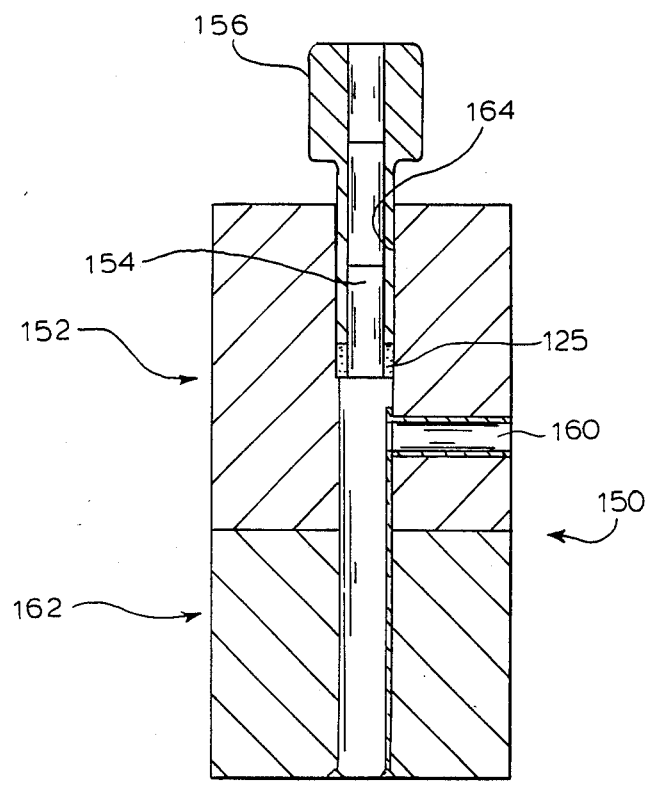
FIG. 7 is a representative device for forming the tablet sleeve of the invention.

Referring now to FIG. 7, a representative device 150 is shown for forming the tablet sleeve of the invention. It should be understood that this is for illustration only and that other devices may be used for compacting representative powders to the desired density. Thus, a die 152 is shown positioned on spacer 162, through the aid of locater pin 154. Pin 154 is retained in die 152 by means of set screw 160. The pin 154 is positioned centrally in bore 164 for forming the tablet sleeve 125 of the invention in cooperation with a tamper 156. It will be understood, that the density of the tablet sleeve 125 formed by such a device will increase with the number of times the tamper 156 is utilized for pressing the powder into its condensed tablet arrangement. A representative size of the tablet sleeve is 0.180 inches in diameter.

Preferably, the fit between the housing chamber 51a diameter and the tablet sleeve 125 diameter is within the range of between about 0.003 inches interference-0.008 inches clearance, and preferably within the range of between about 0.001-0.005 inches clearance. With respect to the laminate as described in the embodiment shown in FIG. 5, the range is within the range of between about 0.001 inches clearance-0.07 inches interference, and preferably within the range of between about 0.02-0.04 inches interference. The clearance dimensions allow for the initial air bleed procedure prior to the swelling of the water absorbing material in accordance with the invention, particularly as it relates to the tablet embodiment.

Thus, as will be appreciated from the above discussion, a blood collecting needle assembly is provided in accordance with this invention for collecting single and multiple samples of blood from a single vein entry, as required, in combination with an arrangement for indicating vein entry to the user of the assembly. In this connection, it will be appreciated that in any form of the invention, the laminate or tablet sleeve type arrangement serves to "flash" the presence of blood in the chamber of the assembly since the presence of blood in the sleeve will be shown through the transparent or translucent housing walls. The material, depending upon its dimension, its compression and/or density, in accordance with this invention, will immediately absorb the water content of the blood and swell to the point of sealing off the chamber in the housing from any leakage of blood. This is almost immediately after a venting of any residual air in the housing chamber in order to allow the flow of intravenous blood from a source into the housing chamber.

Thus, there is almost an instantaneous, simultaneous bleeding of displaced air from the chamber followed by a sealing off of that chamber and a flashing or indication to the user that proper entry has been made to a patient's vein for obtaining the multiple samples. Subsequent to this indication, the user may then insert, sequentially, a plurality of evacuated tubes 16 onto the negative pressure cannula 15 with the sleeve valve 80 providing a self-sealing arrangement between the sequential removal and insertion of additional evacuated tubes 16 for taking the multiple samples of blood from the single source in a single entry into the vein.

The arrangement herein, is, of course, a throw-away device. Once the single or multiple samples have been taken from the single source, it is discarded. It is important, in this connection, to understand that the arrangement herein is a very inexpensive simplified arrangement wherein the separate sleeve may be mounted between the two hubs forming the housing in accordance herewith as a separate piece of the assembly in a mass production line for producing literally thousands of an assembly in accordance with this invention in a rapid efficient highly mechanized manner. Nevertheless, the devices, though they are inexpensive throw-away type devices, function correctly and precisely for indicating vein entry, bleeding off displaced air, and providing appropriate positive sealing off of the chamber of the housing, once vein entry has been indicated by the device.

While the methods and forms of apparatus herein described constitute preferred embodiments of the invention, it is to be understood that the invention is not limited to these precise methods and forms of apparatus, and that changes may be made therein without departing from the scope of the invention which is defined in the appended claims.

What is claimed is:

1. A needle assembly for collecting one or more liquid samples from a source for subsequent discharge into evacuated containers, comprising
   (a) a housing having a forward end and a rearward end;
   (b) a sample collection chamber in said housing;
   (c) a first access opening in said forward end in liquid flow communication with said chamber;
   (d) a first cannula extending outwardly from said first access opening for insertion into said source;
   (e) a second access opening in said rearward end in flow communication with said chamber;
   (f) a second cannula positioned in said second access opening and in flow communication with said chamber;
   (g) valve means on said cannula for controlling discharge of liquid samples from said chamber into evacuated containers attached to said second cannula;
   the improvement characterized by
   (h) cooperating means on said forward end and said rearward end of said housing providing a fluid bleed passage means therebetween, said fluid bleed passage being separate from said flow communication between said chamber and said second access opening;
   (i) vent means in said housing providing flow communication with said fluid bleed passage and ambient;
   (j) swelling means in said fluid bleed passage responsive to aqueous containing materials passing therethrough for swelling and mechanically closing said fluid bleed passage upon contact with an aqueous containing material passing therethrough;
   (k) said swelling means only partially occupying said fluid bleed passage prior to contact with an aqueous containing material;
   (l) whereby when said first cannula engages said source, aqueous containing liquid enters said chamber, forcing any gas therein through said fluid bleed passage and said vent means, causing said liquid to come into contact with said swelling means which swells and mechanically closes said fluid bleed passage.

2. The apparatus of claim 1, further characterized by said cooperating means comprising
   (a) an integral cylindrical extension on said rear end of said housing;
   (b) an integral annular extension on said front end of said housing;
   (c) the internal surface of said front end extension cooperating with the external surface of said rear end extension to form an annular fluid bleed passage means therebetween.

3. The apparatus of claim 1, further characterized by
   (a) aid swelling means is a hydrolyzed starch-polyacrylonitrile graft copolymer with side chains containing carboxamide and carboxylate groups.

4. The apparatus of claim 1, further characterized by said swelling means comprising a laminate, said laminate characterized by
   (a) a central layer of starch-polyacrylonitrile graft copolymer with side chains containing carboxamide and carboxylate groups;
   (b) an outer layer on each side of said central layer;
   (c) said outer layers comprised of non-woven fluid permeable sheets; and
   (d) said laminate positioned in said bleed passage means.

5. The apparatus of claim 2, further characterized by said swelling means comprising
   (a) an annular compressed tablet of hydrolyzed starch-polyacrylonitrile graft copolymer with side chains containing carboxamide and carboxylate groups; and
   (b) said tablet positioned in said bleed passage means.

6. The apparatus of claim 5, further characterized by
   (a) said annular tablet is comprised of powder compressed to a density of about 2.2 grams per cubic centimeter.

7. The apparatus of claim 5, further characterized by
   (a) the clearance fit between said compressed tablet and the walls of said bleed passage containing said tablet is within the range of between about 0.003 inches interference and 0.008 inches clearance.

8. The apparatus of claim 7, further characterized by
   (a) said clearance fit is within the range of between about 0.001 inches clearance and 0.005 inches clearance.

9. The apparatus of claim 2, further characterized by said swelling means comprising
   (a) a laminate formed of three layers into an annular form;
   (b) said laminate consisting of
      (1) a central layer of a starch-polyacrylonitrile graft copolymer with side chains containing carboxamide and carboxylate groups;
      (2) a outer layer on each side of said central layer;
      (3) each said outer layer comprised of non-woven fluid permeable sheets.

10. The apparatus of claim 9, further characterized by
    (a) the longitudinal extent of said annular laminate is within the range of between 0.08 inches and 0.10 inches.

11. The apparatus of claim 1, further characterized by
    (a) said housing including means for connecting a holder for an evacuated container.

12. The apparatus of claim 11, further characterized by
    (a) a holder for an evacuated container connected to said housing.

13. The apparatus of claim 1, further characterized by
    (a) said housing including means for viewing the contents of said chamber.

14. The apparatus of claim 13, further characterized by
    (a) said viewing means is transparent or translucent housing walls adjacent said chamber.

* * * * *